(12) United States Patent
Wakshull et al.

(10) Patent No.: US 6,413,715 B2
(45) Date of Patent: *Jul. 2, 2002

(54) β(1-3)-GLUCAN DIAGNOSTIC ASSAYS

(75) Inventors: Eric M. Wakshull, Princeton; William M. Mackin, Charlton; Janet W. Zimmerman, Harvard; Leslie W. Fisette, Hubbardston, all of MA (US)

(73) Assignee: The Collaborative Group, Stony Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/883,971

(22) Filed: Jun. 19, 2001

Related U.S. Application Data

(63) Continuation of application No. 09/491,719, filed on Jan. 27, 2000, which is a continuation of application No. 08/990,125, filed on Dec. 12, 1997, now Pat. No. 6,084,092, which is a continuation-in-part of application No. PCT/US97/07445, filed on May 1, 1997, which is a continuation-in-part of application No. 08/797,696, filed on Jan. 31, 1997, now Pat. No. 6,110,692.

(51) Int. Cl.[7] .......................... C12Q 1/00; G01N 33/53; G01N 33/566; C07H 1/00; C07H 5/04

(52) U.S. Cl. .............................. 435/4; 435/7.2; 435/7.1; 536/123.12; 536/123.1; 536/55.1; 436/501

(58) Field of Search .............................. 435/4, 975, 7.2, 435/7.1; 536/123.12, 123.1, 55.1; 436/501

(56) References Cited

U.S. PATENT DOCUMENTS

| | | | |
|---|---|---|---|
| 5,032,401 A | 7/1991 | Jamas et al. | 424/425 |
| 5,089,479 A | 2/1992 | Krivan et al. | 514/25 |
| 5,156,948 A | 10/1992 | Christensen et al. | 435/5 |
| 5,217,715 A | 6/1993 | Krivan et al. | 424/92 |
| 5,225,330 A | 7/1993 | Ginsburg et al. | 435/7.32 |
| 5,242,800 A | 9/1993 | Jimenez et al. | |

(List continued on next page.)

FOREIGN PATENT DOCUMENTS

| | | |
|---|---|---|
| EP | 0 133 170 | 2/1985 |
| EP | 0 598 903 | 6/1994 |
| EP | 0 805 161 | 11/1997 |
| JP | 22 50834 | 10/1990 |
| JP | 04 346791 | 12/1992 |
| JP | 80 54388 | 2/1996 |
| WO | 91/93495 | 3/1991 |
| WO | 94/04163 | 3/1994 |
| WO | 97/41439 | 11/1997 |

OTHER PUBLICATIONS

Abel, G. and Czop, J.K., "Stimulation of Human Monocyte β-Glucan Receptors by Glucan Particles Induces Production of TNF–α and IL–1β," *Intl. J. Immunopharmacol.*, 14(8): 1363–1373 (1992).

Adams, et al., "PGG–Glucan Activates NF–κB– like and NF–IL–6–like Transcription Factor Complexes in a Murine Monocytic Cell Line," *J. Leukocyte Biol.*, 62:865–873 (1997).

(List continued on next page.)

Primary Examiner—Louise N. Leary
(74) Attorney, Agent, or Firm—Darby & Darby

(57) ABSTRACT

Methods of isolating β(1–3)-glucan or β(1–3)-glucan-containing organisms in a sample, or of detecting the presence of β(1–3)-glucan or β(1–3)-glucan-containing organisms in a sample, utilizing binding agents for β(1–3)-glucan, such as LacCer, GalCer, globotriaosylceramide and asialoganglioside-GM1, are described. Methods of diagnosing fungal infection, by detecting β(1–3)-glucan or β(1–3)-glucan-containing organisms, are also described. Antibodies and kits useful in the methods are also disclosed.

2 Claims, 4 Drawing Sheets

U.S. PATENT DOCUMENTS

| | | | |
|---|---|---|---|
| 5,266,461 A | | 11/1993 | Tanaka et al. ............. 435/7.32 |
| 5,386,027 A | | 1/1995 | Krivan et al. ............ 536/123.1 |
| 5,389,521 A | | 2/1995 | Krivan et al. .............. 435/7.33 |
| 5,389,547 A | | 2/1995 | Tanaka et al. ................ 436/94 |
| 5,488,040 A | | 1/1996 | Jamas et al. |
| 5,529,904 A | | 6/1996 | Ginsberg et al. ........... 435/7.32 |
| 5,550,030 A | | 8/1996 | Tanaka et al. |
| 5,571,683 A | | 11/1996 | Nakajima et al. ............. 435/14 |
| 6,084,092 A | * | 7/2000 | Wakshull et al. ............ 435/7.2 |
| 6,090,938 A | * | 7/2000 | Wakshull et al. ...... 536/123.12 |
| 6,110,692 A | * | 8/2000 | Wakshull et al. ............ 435/7.2 |
| 6,294,321 B1 | * | 9/2001 | Wakshull et al. .............. 435/4 |

OTHER PUBLICATIONS

Albert S. Baldwin, Jr., "The NF–κ and IκB Proteins: New Discoveries and Insights," *Annu. Rev. Immunol.*, 14:649–683 (1996).

Backenson, et al., "*Borrelia burgdorferi* Shows Specificity of Binding to Glycosphingolipids," *Infec. Immun.*, 63(8):2811–2817 (1995).

Baker, et al., "Glycosphingolipid Receptors for *Pseudomonas aeruginosa*" *Infec. Immun.*, 58(7):2361–2366 (1990).

Bhunia, et al., "Lactosylceramide Stimulates Ras–GTP Loading, Kinases (ME, Raf), p44 Mitogen–activated Protein Kinase, and c–fos Expression in Human Aortic Smooth Muscle Cells," *J. Biol. Chem.*, 271(18):10660–10666 (1996).

Brunke–Reese and Mackin, "Enhanced Nitric Oxide (NO) Production by Peritoneal Macrophages Isolated From Rats Treated with PGG–glucan, (BETAFECTIN™)," *FASEB J.*, 8:A216, Abstact No. 1244 (1994).

Cain et al., "Role of Complement Receptor Type Three and Serum Opsonins in the Neutrophil Response to Yeast," *Complement*, 4:75–86 (1987).

Chatterjee, S., "Lactosylceramide stimulates aortic smooth muscle cell proliferation," *Biochem. And Biophy. Research Comm.*, 181(2):554–561 (1991).

Chatterjee, S. "Regulation of synthesis of lactosylceramide in normal and tumor proximal tublular cells," *Biochem. Biophys. Acta*, 1167:339–344 (1993).

Chatterjee, S. "Role of lactosylceramide and MAP kinase in the proliferation of proximal tubular cells in human polycystic kidney disease," *J. Lipid Research* 37:1334–1343 (1996).

Chatterjee, et al., "Accumulation of glycosphingolipids in human atherosclerotic plaque and unaffected aorta tissues," *Glycobiology*, 7(1):57–65 (1997).

Czop, J.K. and Kay, J., "Isolation and Characterization of β–Glucan Receptors on Human Mononuclear Phagocytes," *J. Exp. Med.*, 173(6):1511–1520 (1991).

Czop, et al., "Perturbation of β–Glucan Receptors on Human Neutrophils Initiates Phagocytosis and Leukotriene $B_4$ Production," *J. Immunol.*, 141(9):3170–3176 (1988).

Czop, et al., "Production and Isolation of Rabbit Anti–Idiotypic Antibodies Directed Against the Human Monocyte Receptor for Yeast β–Glucans," *J. Immunol.*, 145(3):995–1001 (1990).

Diamond, et al., "The I Domain is a Major Recognition Site on the Leukocyte Integrin Mac–1 (CD11b/CD18) for Four Distinct Adhesion Ligands," *J. Cell. Biol.*, 120(4):1031–1043 (1993).

Doita, et al., "Effect of Soluble Aminated β–1, 3–D–Polyglucose on Human Monocytes: Stimulation of Cytokine and Prostaglandin $E_2$ Production but not Antigen–Presenting Function," *J. Leuk. Biol.*, 49:342–351 (1991).

Engstad and Robertsen, "Specificity of a β–Glucan Receptor on Macrophages from Atlantic Salmon (*Salmo salar L.*)," *Dev. Comp. Immunol.*, 18(5):397–408 (1994).

Fukuda, et al., "Structures of Glycosphingolipids Isolated from Human Granulocytes," *J. Biol. Chem.*, 260(2):1067–1082 (1985).

Gallin, et al., "Comparative Effects of Particulate and Soluble Glucan on Macrophages of C3H/HeN and C3H/HeJ Mice," *In. J. Immunopharmacol.*, 14(2):173–183 (1992).

Goldman, R., "Induction of a β–1, 3–D–glucan receptor in P388D1 cells treated with retinoic acid or 1, 25–dihydroxyvitamin $D_3$," *Immunology*, 63(2):319–324 (1988).

Goldman R., "Characteristics of the β–Glucan Receptor of Murine Macophages," *Exp. Cell. Res.*, 174(2):481–490 (1988).

Hossain, M.A., et al., "Comparison Between Wako–WB003 and Fungitec G Tests for Detection of (1–3)–β–D–Glucan in Systemic Mycosis," *J. Clin. Laboratory Analysis*, 11:73–77 (1997).

James, S., et al., "A Novel Class of Macrophage–Activating Immunomodulators," In *Polymeric Drugs and Drug Delivery Systems*, R. L Dunn and R.M. Ottenbrite, eds., (Washington, D.C.: American Chemical Society) pp. 44–51 (1991).

Janusz, et al., "Isolation of soluble Yeast β–Glucans that Inhibit Human Monocyte Phagocytosis Mediated by β–Glucan Receptors," *J. Immunol.*, 137(10):3270–3276 (1986).

Jimenez–Lucho, et al., "*Cryptococcus neoformans, Candida Albicans,* and Other Fungi Bind Specifically to the Glycosphingolipid Lactosylceramide (Galβ1–4Glcβ1–1Cer), a Possible Adhesion Receptor for Yeasts," *Infec. Immun.*, 58(7):2085–2090 (1990).

Karlsson, Karl–Anders, "Animal Glycosphingolipids as Membrane Attachment Sites for Bacteria," *Annu. Rev. Biochem.*, 58:309–350 (1989).

Konopski, et al., "A Novel Immunomodulator Soluble Aminated β–1, 3–D–Glucan: Binding Characteristics to Mouse Peritoneal Macrophages," *Biochem. Biophys. Acta*, 1221(1):61–65 (1994).

Konopski, et al., "A novel immunomodulator soluble aminated beta–1, 3–D–glucan: binding characteristics to mouse peritoneal macrophages," *Chemical Abstracts*, 120(17) (1994).

Konopski, Z., "Interferon–γ Inhibits Endocytosis of Soluble Animated β–1,3–D–Glucan and Neutral Red in Mouse Peritoneal Macrophages," *Journal of Interferon and Cytokine Research* 15:597–603 (1995).

Konopski, et al., "IFN–gamma inhibits internalization of soluble aminated beta–1,3–D–glucan by macrophages and thereby down–regulates the glucan induced release of TNF–alpha and IL–1 beta," *Chemical Abstract*, 121(13) (1994).

Lund–Johnson, et al., "Activation of Human Phagocytes Through Carbohydrate Antigens (CD15, Sialyl–CD15, CDw17, and CDw65)," *J. Immunol.*, 148:3221–3229 (1992).

Mackin, et al., "Enhanced Microbicidal Activities of Human Peripheral Blood Monocytes and Neutrophils (PMN) After Pretreatment with PGG–glucan, (BETAFECTIN™)," *FASEB J.*, 8:A488, Abstract No. 2827 (1994).

Mills A. and Duggan, M.J., "Orphan seven transmembrane domain receptors: reversing pharmacology," *Trends in Biotechnology* 12:47–49 (1994).

Miyazaki, T., et al., "Plasma (1–3)–β–D–Glucan and Fungal Antigenemia in Patients with Candidemia, Aspergillosis, and Cryptococcosis," *J. of Clin. Microbiology*, 33(12):3115–3118 (1995).

Mori, T., et al., "Evaluation of Plasma (1–3)–β–D–Glucan Measurement by the Kinetic Turbidimetric Limulus Test, for the Clinical Diagnosis of Mycotic Infections," *Eur. J. Clin. Chem. Clin. Biochem.*, 35(7):553–560 (1997).

Morita, T., et al., "A New (1–3)–β–D–Glucan Mediated Coagulation Pathway Found in Limulus Amebocytes," *Elsevier/North–Holland Biomedical Press*, 129(2):318–321 (1981).

Müller, et al., "Receptor Binding and Internalization of Water–Soluble (1–3)–β–D–Glucan Biologic Response Modifier in Two Monocyte/Macrophage Cell Lines," *J. Immunol.*, 156:3418–3425 (1996).

Müller, et al., "Functional β–glucan receptor expression by a microglial cell line," *Res. Immunol.*, 145:267–275 (1994).

Poutsiaka, et al., "Cross–Linking of the β–Glucan Receptor on Human Monocytes Results in Interleukin–1 Receptor Antagonist but Not Interleukin–1 Production," *Blood*, 82(12):3695–3700 (1993).

Sandberg, et al., "Putative Glycoprotein and Glycolipid Polymorphonuclear Leukocyte Receptors for the *Actinomyces naeslundii* WVU45 Fimbrial Lectin," *Infec. And Immun.*, 63(7):2625–2631 (1995).

Schütze, S., et al., "The role of diacylglycerol and ceramide in tumor necrosis factor and interleukin–1 signal transduction," *J. of Leukocyte Biology*, 56:533–541 (1994).

Stevens, et al., "Lactosylceramide in inflammatory bowel disease: a biochemcial study," *Gut*, 29:580–587 (1988).

Stewart, R.J. and Boggs, J.M., "A Carbohydrate Interaction Between Galactosylceramide–Containing Liposomes and Cerebroside Sulfate–Containing Liposomes: Dependence on the Glycolipid Ceramide Compositions," *Biochemistry* 32:10666–10674 (1993).

Strömberg, et al., "Studies on the binding of bacteria to glycolipids–Two species of Propioinibacterium apparently recognize separate epitopes on lactose of lactosylcermide," FEBS Letters, 232(1):193–198 (1988).

Symington, F., "CDw17:A Neutrophil Glycolipid Antigen Regulated by Activation," *J. Immunol.*, 142(8):2784–2790 (1989).

Szabó, et al., "Biochemical Properties of the Ligand–binding 20kDa Subunit of the β–Glucan Receptors on Human Mononuclear Phagocytes," *J. Biol. Chem.*, 270(5):2145–2151 (1995).

Tamura, H., et al., "Plasma (1–3)–β–D–Glucan Assay and Immunohistochemical Staining of (1–3)–β–D–Glucan in the Fungal Cell Walls Using a Novel Horseshoe Crab Protein (T–GBP) that Specifically Binds to (1–3)β–D–Glucan," *J. of Clin. Laboratory Analysis*, 11:104–109 (1997).

Thornton, et al., "Analysis of the Sugar Specificity and Molecular Location of the β–Glucan–Binding Lectin Site of Complement Receptor Type 3 (CD11b/CD18)," *J. Immunol.*, 156(3):1235–1246 (1996).

Tsuruoka, et al., "Selection of a Mutant Cell Line Based on Differential Expression of Glycophingolipid, Utilizing Anti-lactosylcermaide Antibody and Complement," *J. Biol. Chem.*, 268(3):2211–2216 (1993).

Ullrich, A. and Schlessinger, J., "Signal Tranduction by Receptors with Tyrosine Kinase Activity," *Cell* 61:203–212 (1990).

Wakshull, et al., "Synergistic Stimulation of Myeloid Progenitor Cell Proliferation by a Novel β–Glucan and GM–CSF," *J. Cell Biochem. Suppl.*, 18:A222 (1994).

Wakshull, et al., "Characterization PCC–Glucan Binding to a β–Glucan Receptor on Human Leukocytes," *FASEB J.*, 10:A1338, Abstract No. 1954 (1996).

Williams, D.L. and Quillen, J.H., "Overview of (1–3)–β–D–Glucan Chemistry, Immunology and Toxicology," Paper presented at the Beltwide Cotton Conference, Nashville, TN (1996).

Yamamoto, et al., "Binding Specificity of Lactobacillus to Glycolipids," *Biochem. And Biophys. Research comm.*, 228:148–152 (1996).

Zimmerman, et al., "A Novel Carbohydrate–Glycosphingolipid Interaction between a β–(1–3)–Glucan Immunomodulator, PGG–glucan, and Lactosylceramide of Human Leukocytes," *J. Biol. Chem.*, 273(34):22014–22020 (1988).

* cited by examiner

β(1-3)-GLUCAN DIAGNOSTIC ASSAYS

RELATED APPLICATIONS

This application is a continuation of application Ser. No. 09/491,719 filed Jan. 27, 2000, which is a cntinuation of Ser. No. 08/990,125 filed Dec. 12, 1997, now U.S. Pat. No. 6,084,092, which is a continuation-in-part of PCT/US97/07445, filed May 1, 1997, which is a continuation-in-part of Ser. No. 08/797,696, filed Jan. 31, 1997, now U.S. Pat. No. 6,110,692. The teachings of the prior applications are incorporated herein in their entirety.

BACKGROUND OF THE INVENTION

Immunocompromised patients are susceptible to a variety of neoplastic, protozoal, viral, bacterial and fungal diseases; of these, bacterial, viral and fungal infections result in the greatest mortality (Bartlett, M. and J. Smith, *Clin. Microbiol. Rev.* 4:137 (1991); Bodey, G. et al., *Dur. J. Clin. Microbiol. Infect. Dis.* 11:99 (1992); Sternberg, S., *Science* 266:1632 (1994); Cox, G. and J. Perfect, *Curr. Opin. Infect. Dis.* 6:422 (1993); Deepe, G. and W. Bullock, *Dur. J. Clin. Microbiol. Infect. Dis.* 9:377 (1990); Fox, J. L., *ASM News* 59:515 (1993); Kujath, P., *Mycoses* 35:225 (1992); Pfaller, M. and R. Wenzel, *Dur. J. Clin. Microbiol. Infect. Dis.* 11:287 (1992); and Samonis, G. and D. Bafaloukos, In vivo 6:183 (1992)). Systemic fungal infections are now an important medical problem in the care of immunocompromised patients. Fungal infections in immunocompromised patients are mainly the result of opportunistic infections by normally harmless, asymptomatic commensals, which can be pathogenic under certain conditions (Odd, J., *Antimicrob. Chemother.* 31:463 (1993); Rhodes, J. et al., *J. Med. Vet. Myc.* 20:113 (1992); Saral, R. *Rev. Infect. Dis.* 13:487 (1991)). Species of Cryptococcus, Candida, Coccidioides, Histoplasma, Blastomyces, Sporothrix and Aspergillus, as well as other opportunistic fungi, are important causative agents; of these, Candida species, especially *C. albicans*, are the most common. Candidemia accounts for 8–10% of all hospital-acquired bloodstream infections and Candida species are the fourth most common cause of nosocomial septicemias. Mortality rates associated with systemic Candida infections are estimated to be as high as 50% of infected patients. Infections caused by other types of fungi (e.g., Aspergillus, Cryptococcus) are also common in immunocompromised patients and carry significant treatment costs and mortality levels (Meunier, F., *Amer. J. Med.* 99 (Suppl. 6A):60S–67S (1995)).

A variety of approaches have been used to diagnose fungal infections in humans; each method has distinct limitations. Blood cultures often fail to detect existing infections and may take two to five days to detect fungal growth, a period of time which an infected patient often cannot survive. Assays for fungal-specific metabolites are also used. For example, an assay for D-arabinitol can be performed by monitoring of oxidation of D-arabinitol by D-arabinitol dehydrogenase (Soyama, K. and E. Ono, *Clin. Chim. Acta* 149:149 (1985); Soyama, K. and E. Ono, *Clin. Chim. Acta.* 168:259 (1987)). However, D-arabinitol dehydrogenase also reacts with D-mannitol naturally existing in serum samples, resulting in an artificially high oxidation rate. Furthermore, both D-mannitol and D-arabinitol are elevated during renal failure (Reiss, E. and C. Morrison, *J. Clin. Microbiol. Rev.* 6:311–322 (1993)).

Immunoassays to detect antibody binding to a fungal marker antigen have also been developed: for example, an assay for enolase secreted by *C. albicans* is described (Matthews, R. C. et al., *Lancet i:*1415 (1984), Matthews, R. C. et al., *J. Clin. Microbiol.* 26:459 (1988), and Walsh, et al., *New. Engl. J. Med.* 324:1026 (1991)). However, the capture antibody is believed to react with enolases from sources other than *C. albicans* (Reiss, E. and C. Morrison, *J. Clin. Microbiol. Rev.* 6:311–322 (1993), and the sensitivity is limited (Mitsutake, K. et al., *J. Clin. Microbiol.* 34:1918–1921 (1996)). Another assay uses detection of aspartyl proteinase secreted from *C. albicans* (Staib, R., Sabouraudia 4:187 (1965); Reiss, E. and C. J. Morrison, *Clin. Microbiol. Rev.* 6:311 (1993)). An assay to detect secreted β(1–3)-glucan, based on activation of factor G of the Limulus coagulation enzyme cascade, is also described (U.S. Pat. No. 5,266,461); however, this assay is sensitive to a number of interfering compounds, including compounds of fungal origin (Matsumoto, T. M. et al., *Urol. Res.* 21:21–117–120 (1993)).

Additional assays include immunological assays to detect antigens, such as cell-wall mannan, circulating through the host during fungal infection, by radioimmunassay (RIA) (Weiner, M. H. and M. Coats-Stephen, *J. Infect. Dis.* 140:989 (1979) ), inhibition enzyme immunoassay (Meckstroth, K. L. et al., *J. Infect. Dis.* 144:24 (1981); Segal, E. et al., *J. Clin. Microbiol.* 10:116–118 (1979)), and double antibody sandwich enzyme immunoassay (Lew, M. A. et al., *J. Infect. Dis.* 145:45–56 (1982)). Reliability of these tests may be hampered by the presence of anti-mannan antibodies and cell-wall binding proteins. Furthermore, the concentration of the antigen is low, even with severe infection, so detection can be difficult.

Amplification of sample DNA by polymerase chain reaction (PCR) has been used with fungal-specific nucleotide probes to detect the presence of fungal DNA (U.S. Pat. Nos. 5,489,513; 5,426,027; and 5,324,632). These methods are complicated, expensive, time-consuming and often are sensitive to interfering materials found in the host sample (Reiss, E. and C. Morrison, *J. Clin. Microbiol. Rev.* 6:311–323 (1993)).

Thus, each of the variety of methods for diagnosing fungal infection has deficiencies, including unreliability, interfering agents, or a need for sophisticated equipment or trained personnel. Because of the increasing incidence of fungal infections, a need remains for accurate, simple, quantitative and expedient methods for diagnosis of fungal infections.

SUMMARY OF THE INVENTION

The present invention is drawn to methods of isolating, concentrating or purifying β(1–3)-glucans, as well as β(1–3)-glucan-containing organisms, and also to assays to quantify the amount of β(1–3)-glucans, or β(1–3)-glucan-containing organisms in a test sample. The test sample can be a liquid or a solid, and can originate from various sources, including complex animal sources (e.g., a biological fluid, such as blood, serum, plasma, urine, feces, mucus, sputum, bile, ascites fluid, wound secretions, vaginal excretions, synovial fluid, cerebrospinal fluid, peritoneal lavage fluid, lung lavage fluid, ocular fluid, saliva or whole tissue extract; alternatively, the test sample can be solid specimen, such as skin or other tissue); plant sources (plant tissue, plant tissue extract, fruit or fruit extracts, seeds or seed extracts, sap, or homogenates); bacterial cells; viral cells; fungal cells; tissue cultures; environmental sources; food sources; or fermentation process sources.

In the methods of the invention, a β(1–3)-glucan binding agent is used to capture or purify β(1–3)-glucans and/or β(1–3)-glucan-containing organisms from a test sample. β(1–3)-glucan binding agents are compounds that have an affinity for underivatized, aqueous soluble β(1–3)-glucan, including lactosyl ceramide (LacCer) (human), LacCer (bovine), LacCer (porcine), galactosyl ceramide (GalCer) I, GalCer II, globotriaosyl ceramide (globotriaosylCer), and asialoganglioside-GM1. The β(1–3)-glucan binding agent (s), or the test sample, can be coupled or attached to a solid phase or a fluid phase. The test sample is contacted with a β(1–3)-glucan binding agent, under conditions that are suitable for binding of any β(1–3)-glucan that may be present in the test sample to the β(1–3)-glucan binding agent; resultant complexes of β(1–3)-glucan and β(1–3)-glucan binding agent ("primary complexes") can then be isolated, in order to isolate β(1–3)-glucan. In another embodiment, the primary complexes can be detected, in order to detect β(1–3)-glucan or β(1–3)-glucan-containing organisms in the test sample: the presence of primary complexes is indicative of the presence of β(1–3)-glucan or β(1–3)-glucan-containing organisms. In another embodiment, the presence of β(1–3)-glucan can be detected through a competition assay, in which labeled underivatized, aqueous soluble β(1–3)-glucan and β(1–3)-glucan binding agents are incubated with the test sample; the amount of β(1–3)-glucan in the test sample is inversely proportional to the amount of complexes of labeled underivatized, aqueous soluble β(1–3)-glucan and β(1–3)-glucan binding agents. The presence of β(1–3)-glucan (or of β(1–3)-glucan-containing organisms) in the test sample is indicative of a fungal infection or fungal contamination. Antibodies that can be used in these methods and assays, as well as kits that can be used in these methods and assays, are also within the scope of the invention.

The methods and assays of the invention allow for specific, highly sensitive detection of β(1–3)-glucans in a test sample, facilitating diagnosis of fungemias and detection of fungal contamination, without requiring expensive equipment or trained personnel.

DETAILED DESCRIPTION OF THE FIGURES

FIG. 1 is a graphic illustration of a comparison of underivatized, aqueous soluble β(1–3)-glucan and single helix β(1–3)-glucan (single helix) competition of $^3$H-underivatized, aqueous soluble β(1–3)-glucan binding in three assay formats. Underivatized, aqueous soluble β(1–3)-glucan or single helix glucan was used at designated concentrations to compete for $^3$H-underivatized, aqueous soluble β(1–3)-glucan binding to lactosyl ceramide (LacCer) in a 96-well plate (triangles), or to lactosyl ceramide in reconstituted membranes (squares), or to human leukocyte membranes (HLM) (circles). Open symbols represent underivatized, aqueous soluble β(1–3)-glucan, and closed symbols represent single helix. Maximum competition was assigned at the highest concentration of underivatized, aqueous soluble β(1–3)-glucan used as competitor in each type of assay.

FIG. 2 is a graphic illustration of data showing that underivatized, aqueous soluble β(1–3)-glucan and high molecular weight underivatized, aqueous soluble β(1–3)-glucan (very high molecular weight glucan (VHMW glucan) compete more effectively for $^3$H-underivatized, aqueous soluble β(1–3)-glucan binding to lactosyl ceramide (LacCer) in a 96-well plate assay than do single helix or laminarin. Underivatized, aqueous soluble β(1–3) -glucan (circles), single helix (closed squares), laminarin (crosses) and high molecular weight underivatized, aqueous soluble β(1–3)-glucan (VHMW glucan) (hatched squares) were used at designated concentrations to compete for $^3$H-inderivatized, aqueous soluble β(1–3)-glucan binding to lactosyl ceramide (bovine) in a 96-well plate assay. "% control binding" means the percent of binding with no competitor present in the reaction mixture.

DETAILED DESCRIPTION OF THE INVENTION

Figure 1:
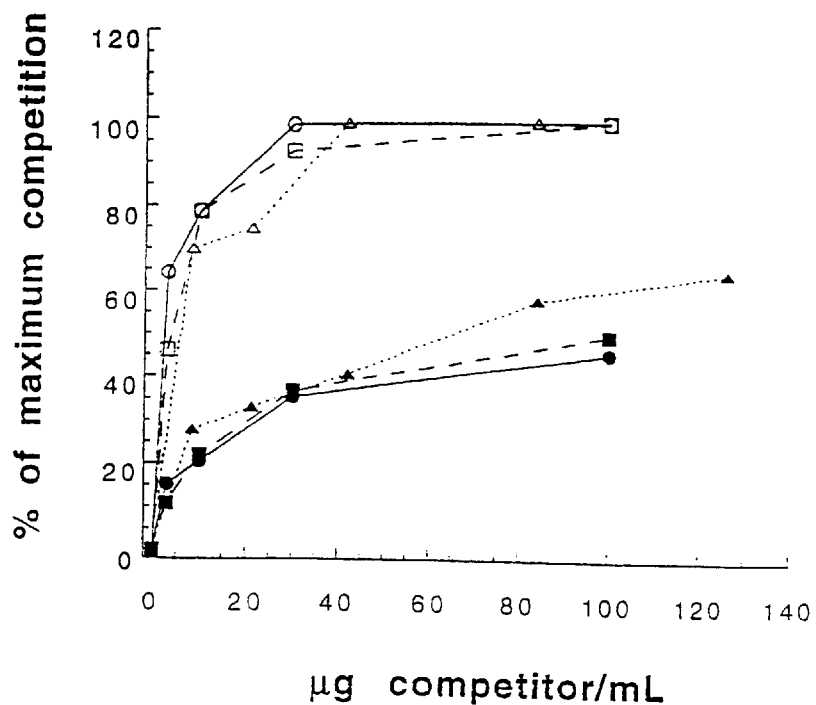

The invention is based on a discovery that several glycosphingolipids exhibit significant specific binding to a component of fungal cell walls, β(1–3)-glucan, and particularly, to $^3$H-underivatized, aqueous soluble β(1–3)-glucan (PGG-Glucan). Underivatized, aqueous soluble β(1–3)-glucans are also described in U.S. Ser. Nos. 08/400,488, 08/432,303, 08/373,251 and 08/469,233 and U.S. Pat. Nos. 5,322,841, 5,488,040, 5,532,223, 5,622,939 and 5,633,369.

The glycosphingolipids include lactosyl ceramides (LacCer), galactosyl ceramides (GalCer), globotriaosyl ceramides, and asialoganglioside-GM1, from various sources. Table 1 sets forth the specific binding of various glycosphingolipids, as assessed by a binding assay in 96-well plates (see Examples for description of Experiments).

TABLE 1

Specific binding of $^3$H-underivatized, aqueous soluble β(1–3)-glucan (PGG-Glucan) to various sphingolipids in a 96-well plate binding assay

| Sphingolipid | $^3$H-PGG-Glucan bound (ng/μg sphingolipid) |
|---|---|
| LacCer (HLM) | 3.14 ± 0.29 |
| LacCer (bovine) | 2.18 ± 0.39 |
| LacCer (porcine) | 2.35 ± 0.23 |
| GalCer I | 1.02 ± 0.32 |
| GalCer II | 3.90 ± 0.14 |
| Ceramides | 0.02 ± 0.01 |
| Sulfatides | 0.00 ± 0.01 |

TABLE 1-continued

Specific binding of ³H-underivatized, aqueous
soluble β(1–3)-glucan (PGG-Glucan) to various
sphingolipids in a 96-well plate binding assay

| Sphingolipid | ³H-PGG-Glucan bound (ng/μg sphingolipid) |
|---|---|
| Sphingosine | 0.02 ± 0.00 |
| Psychosine | 0.09 ± 0.00 |
| Asialoganglioside-GM2 | 0.00 ± 0.01 |
| Globoside | 0.00 ± 0.01 |
| GlobotriaosylCer | 0.84 ± 0.13 |
| Glucocerebrosides (GlcCer) | 0.12 ± 0.03 |
| Asialoganglioside-GM1 | 0.50 ± 0.10 |

These compounds have in common a terminal galactose, which may therefore be involved in binding interactions between ³H-underivatized, aqueous soluble β(1–3)-glucan and the glycosphingolipid. A terminal galactose alone is not sufficient for binding, however, since psychosine (1-galactosyl sphingosine) does not show appreciable binding. This compound lacks the fatty acid portion of ceramide.

While several fatty acid structures in LacCer can support binding of ³H-underivatized, aqueous soluble glucan, as shown with HPLC fractionated LacCer from HLM in Table 2, the carbon-carbon double bond found in C18:1 sphingosine is apparently important for binding, since the commercially available dihydro-sphingosine LacCers do not bind.

TABLE 2

Specific binding of ³H-underivatized, aqueous
soluble β(1–3)-glucan (PGG-Glucan) to LacCer
of defined structures in the 96-well plate
binding assay

|  | Fatty Acid | Long Chain Base | ³H-PGG-Glucan bound (ng/μg LacCer) |
|---|---|---|---|
| LacCer (HLM) | C16:0 | C18:1 | 3.31 |
|  | C18:0 | C18:1 | 1.93 |
|  | C24:2 | C18:1 | 2.01 |
|  | C24:1 | C18:1 | 2.31 |
|  | C22:0 | C18:1 | 3.57 |
|  | C24:0 | C18:1 | 3.14 |
| N-Palmitoyl-DL-dihydrolacto-cerebroside | C16:0 | C18:0 | 0.00 |
| N-Stearoyl-DL-dihydrolacto-cerebroside | C18:0 | C18:0 | 0.00 |
| N-Lignoceroyl-DL-dihydrolacto-cerebroside | C24:0 | C18:0 | 0.00 |

The binding of ³H-underivatized, aqueous soluble β(1–3)-glucan to LacCer was also found to be temperature dependent, similar to that with HLM. Binding occurs at 37° C., but not at 4° C., as indicated in Table 3. The temperature specificity was seen with two different sources of LacCer.

TABLE 3

Temperature dependence of ³H-underivatized,
aqueous soluble β(1–3)-glucan (PGG-Glucan)
specific binding to lactosyl ceramides

|  | Temperature | ³H-PGG-Glucan bound (ng/μg LacCer) |
|---|---|---|
| LacCer (HLM) | 37° C. | 1.76 |
|  | 4° C. | 0.00 |
| LacCer (bovine) | 37° C. | 2.50 |
|  | 4° C. | 0.01 |

Figure 2:
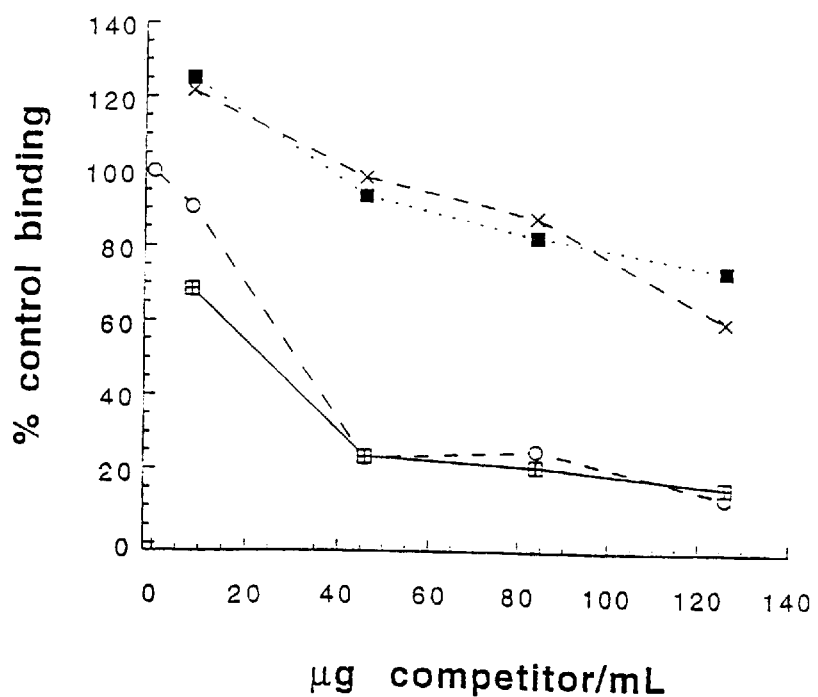

The conformer specificity of competition for ³H-underivatized, aqueous soluble β(1–3)-glucan binding was also similar to that previously described with HLM. As shown in FIG. 1, underivatized, aqueous soluble β(1–3)-glucan competes for ³H-underivatized, aqueous soluble β(1–3)-glucan binding to HLM, and to LacCer in both the 96-well assay and the reconstitution assay to the same degree. In contrast, single helix (SH) glucan does not compete efficiently in any of the assays. Also, Network, a glucan preparation comprising glucan that is primarily in the triple helix conformation and has a molecular weight of greater than one million, competes similarly to underivatized, aqueous soluble β(1–3)-glucan, while laminarin does not compete efficiently for ³H-underivatized, aqueous soluble β(1–3)-glucan binding to LacCer in the 96-well plate assay (see FIG. 2).

From these results, an in vivo binding agent for underivatized, aqueous soluble β(1–3)-glucan is LacCer. Other compounds tested as described above also have an affinity for underivatized, aqueous soluble β(1–3)-glucan; these compounds are also intended to be encompassed by the term "β(1–3)-glucan binding agent" as used herein. From this work, it appears that there are three characteristics which determine the affinity of a compound for underivatized, aqueous soluble β(1–3)-glucan: length of the fatty acid chain of the compound, presence of a terminal galactose in the compound, and presence or absence of a double bond in the sphingosine portion of the compound. Specifically, compounds shown herein to have an affinity for underivatized, aqueous soluble β(1–3)-glucan, have a fatty acid chain of from about 16 to about 24 carbons in length, contain a terminal galactose, and contain a double bond in the sphingosine portion. However, compounds having fatty acid chains of less than 16 and greater than 24 carbons are also contemplated by the term, "β(1–3)-glucan binding agent", provided that they have an affinity for underivatized, aqueous soluble β(1–3)-glucan. Furthermore, as used herein, "terminal galactose" is intended to encompass unmodified galactose as well as derivatized or modified galactose, such as sulphonated galactose. Binding agent mimics or binding agent analogues, that have an affinity for underivatized, aqueous soluble β(1–3)-glucan, are also included within the term, β(1–3)-glucan binding agent. Compounds having these characteristics (the β(1–3)-glucan binding agents) are suitable for use in the assays and methods described herein.

As a result of this discovery, methods are now available to capture, concentrate or purify β(1–3)-glucans, including yeast or fungal soluble β(1–3)-glucans, yeast or fungal insoluble β(1–3)-glucans, as well as to capture, concentrate or purify β(1–3)-glucan-containing organisms. In addition, assays to quantify the amount of β(1–3)-glucan in a test sample are described herein; these assays can be used for diagnosis of fungal infections. Kits useful in the assays and methods are also described. The methods, assays and kits take advantage of the affinity of β(1–3)-glucan binding agents, as described above, for high molecular weight, soluble β(1–3)-glucan.

In accordance with the methods of the invention, a sample known to contain, or thought to contain, fungus or β(1–3)-glucan-containing organisms is obtained. The test sample can be a liquid or a solid, and can originate from various sources, including complex animal sources (e.g., mammalian cells or tissues), plant cells or tissues, bacterial cells, viral cells, fungal cells, tissue cultures, environmental sources, food sources, or fermentation process sources. For example, if the test sample is from an animal source, such as from a human individual suspected of having a fungal infection, the test sample can be a biological fluid, such as blood (whole blood, whole blood serum or whole blood plasma), urine, feces, mucus, sputum, bile, ascites fluid, wound secretions, vaginal excretions, synovial fluid, cerebrospinal fluid, peritoneal lavage fluid, lung lavage fluid, ocular fluid, saliva or whole tissue extract; alternatively, the test sample can be solid specimen, such as skin or other tissue. If the individual suspected of having a fungal infection is immunocompromized, the preferred test sample is a urine sample. If the sample is from a plant source, it can be a fluid or a solid specimen, such as plant tissue, plant tissue extract, fruit or fruit extracts, seeds or seed extracts, sap, or plant homogenates. The test sample can also be an environmental source such as water, soil, or soil extracts, or a food source such as prepared foodstuffs, that may be fungally contaminated. Alternatively, the test sample can be a sample from a fermentation process, such as fermentation broth.

If the test sample is high in protein, a de-proteinating step, such as standard trichloroacetic acid or perchloric acid precipitation methods, or precipitation using a standard 70% ethanol precipitation method can be performed prior to performing the assay of the invention (*Methods in Enzymology* Vol. 182: Guide to Protein Purification (Deutscher, M. P., Ed., Academic Press, Inc, San Diego Calif., 1990), Chapter 22, pp. 285–306). However, such a step is not necessary to perform the methods of the invention.

In a method of the invention, a β(1–3)-glucan binding agent is used to capture or purify β(1–3)-glucans and/or β(1–3)-glucan-containing organisms from a test sample. The term, "β(1–3)-glucan binding agent", as used herein, refers to compounds described above that have an affinity for underivatized, aqueous soluble β(1–3)-glucan, including LacCer (HLM), LacCer (bovine), LacCer(porcine), GalCer (GalCer I, GalCer II, or a combination of GalCer I and GalCer II), globotriaosylCer, and asialoganglioside-GM1. In a preferred embodiment, the β(1–3)-glucan binding agent is LacCer or GalCer II, because of the high affinity of β(1–3)-glucan for these compounds. In another preferred embodiment, the β(1–3)-glucan binding agent is GalCer; "GalCer", as used herein, can be either GalCer I, GalCer II, or a combination of GalCer I and GalCer II. More than one type of β(1–3)-glucan binding agent can also be used concurrently.

In one embodiment of this method of the invention, the β(1–3)-glucan binding agent(s) can be coupled to a solid phase (e.g., filter, membrane such as cellulose or nitrocellulose, plastic (e.g., microtiter plate, dipstick), glass (e.g., slide), bead (e.g., latex beads), particle, organic resin, or other organic or non-organic solid phase) or a fluid (e.g.,TRIS buffer or phosphate buffer) phase. Coupling the β(1–3)-glucan binding agent(s) to the solid or fluid phase can be accomplished by standard methods, including, for example, air drying, heat drying, or chemical reaction. In this embodiment of the method, the test sample is contacted with a β(1–3)-glucan binding agent coupled to a solid or fluid phase, under conditions that are suitable for binding of any β(1–3)-glucan (or β(1–3)-glucan-containing organisms) that may be present in the test sample to the β(1–3)-glucan binding agent. β(1–3)-glucan or a β(1–3)-glucan-containing organism that is bound to a β(1–3)-glucan binding agent is referred to herein as a "primary complex". The formation of primary complexes indicates that β(1–3)-glucan, or a β(1–3)-glucan-containing organism, has been "captured" from the test sample. β(1–3)-glucan or a β(1–3)-glucan-containing organism that has been "captured" from the test sample is the β(1–3)-glucan or the β(1–3)-glucan-containing organism that is bound to a β(1–3)-glucan binding agent.

In another embodiment of this method, the test sample can be attached (e.g., adsorbed, coated, coupled, covalently attached, attached by affinity binding) to a solid support, such as by dipping the solid support into the test sample, by dropwise application of a fluid test sample with the solid support, or by smearing a solid test sample onto the solid support. If desired, the test sample can be mixed with a liquid, such as saline or any other appropriate biological buffer, prior to attachment to the solid support, such as, for example, in the case of solid test samples. After the test sample is attached to a solid support (forming an "attached test sample"); a β(1–3)-glucan binding agent (or more than one type of β(1–3)-glucan binding agent) is contacted with the attached test sample, under conditions that are suitable for binding of any β(1–3)-glucan that may be present in the attached test sample to the β(1–3)-glucan binding agent. β(1–3)-glucan binding agent that is bound to any β(1–3)-glucan or β(1-3)-glucan-containing organism in the attached test sample is also referred to herein as a "primary complex".

In either embodiment of this method, any primary complexes that have formed can be isolated, in order to obtain, to isolate, to concentrate or to purify the β(1–3)-glucan (or β(1–3)-glucan containing organisms) from the test sample. The primary complexes can be obtained or isolated using standard methods, such as by immunoprecipitation or other means, resulting in concentrated or purified primary complexes, from which concentrated or purified β(1–3)-glucan (or β(1–3)-glucan-containing organisms) can be separated using standard methods (see *Current Protocols in Molecular Biology*, Vol. II, Ch. 10 (Ausubel, F. et al., eds., John Wiley & Sons, 1997).

In another embodiment of the invention, the primary complexes can be detected, in an assay to determine whether β(1–3)-glucan (or β(1–3)-glucan-containing organisms) is present in the test sample. In addition, the amount of primary complexes can be determined: the concentration of the primary complexes correlates positively with the quantity of β(1–3)-glucan (or β(1–3)-containing organisms) present in the test sample. A variety of methods can be used to detect, and/or to determine the quantity of, the β(1–3)-glucan, including detection of the β(1–3)-glucan using an agent that selectively binds the primary complex, such as anti-β-glucan antibodies (monoclonal or polyclonal) or antibody fragments; detection of enzymatic reaction precipitated by β(1–3)-glucan, such as by Limulus amebocyte lysate or Limulus lysate Factor G assay (Mori, T. et al., *Eur. J. Clin. Chem. Biochem* 35(7): 553–560 (1997); Hossai, M. A. et al., *J. Clin. Lab. Anal.* 11:73–77 (1997); Obayashi, T. et al., *J. Med. Vet. Mycology* 30:275–280 (1992), the entire teachings of each of which are incorporated herein by reference); use of enzymes that react with β-glucans; or other means. In a preferred embodiment, the Limulus lysate Factor G assay is used. In another embodiment of the method, the primary complexes can be detected through the use of a detectable label on the β(1–3)-glucan binding agent, such as a radionucleotide (e.g., radioimmunoassay), dye, fluorescent compound, biotin or streptavidin. If desired, the quantity of primary complexes can be compared to a standard curve generated with a known β(1–3)-glucan standard.

In another embodiment of the invention, a competition assay can be used to determine the quantity of β(1–3)-glucan (or β(1–3)-glucan containing organisms) that is present in the test sample. For example, labeled (for example, with radionucleotides, dyes, or fluorescent labels) underivatized, aqueous soluble β(1–3)-glucan, or another soluble β(1–3)-glucan, such as VHMW glucan, is incubated with the β(1–3)-glucan binding agent and the test sample, under (conditions suitable for binding of underivatized, aqueous soluble β(1–3)-glucan to its binding agent. Subsequently, the amount of primary complexes containing labelled, underivatized, aqueous soluble β(1–3)-glucan is determined. This amount is compared with the amount of primary complexes generated by incubation of labelled underivatized, aqueous soluble β(1–3)-glucan with the β(1–3)-glucan binding agent in a control sample (i.e., a sample having a known amount of unlabeled β(1–3)-glucan) or a series of control samples (e.g., a standard curve). The amount of β(1–3)-glucan in the test sample is inversely proportional to the amount of primary complexes containing labelled, underivatized, aqueous soluble β(1–3)-glucan.

Detection and quantitation of the presence of β(1–3)-glucan, or of β(1–3)-glucan containing organisms, is useful in the diagnosis of fungemias or fungal contamination. To diagnose fungal infection in an individual, for example, a sample, such as a biological fluid sample, is obtained from the individual. The sample is assayed for the presence of β(1–3)-glucan, as described in detail above. The presence of β(1–3)-glucan in the test sample is indicative of the presence of a component of fungal cell walls, and is therefore indicative of fungal presence, contamination, or infections. Similarly, the presence of β(1–3)-glucan in a sample from an environmental source, or a food source, is indicative of fungal presence or contamination. In addition, quantitation of the amount of β(1–3)-glucan, or of β(1–3)-glucan containing organisms, can provide information regarding the severity of the infection or contamination. The methods and assays of the invention provide accurate and specific identification of the presence of β(1–3)-glucans in a test sample, thereby facilitating diagnosis and treatment of fungal infection and contamination.

Antibodies to β(1–3)-glucan that are useful in the methods and assays described above are also contemplated in the invention. Monoclonal or polyclonal antibodies can be produced using enriched or purified β(1–3)-glucan preparations by standard techniques. For instance, polyclonal and/or monoclonal antibodies which bind to β(1–3)-glucan are within the scope of the invention. A mammal, such as a mouse, rat, hamster or rabbit, can be immunized with an immunogenic form of the β(1–3)-glucan (i.e., an form that is capable of eliciting an antibody response). Techniques for conferring immunogenicity include conjugation to carriers or other techniques well known in the art. The β(1–3)-glucan can be administered in the presence of an adjuvant. The progress of immunization can be monitored by detection of antibody titers in plasma or serum. Standard ELISA or other immunoassays can be used with the immunogen as antigen to assess the levels of antibody. Following immunization, antisera can be obtained, and if desired, polyclonal antibodies can be isolated from the serum. Monoclonal antibodies can also be produced by standard techniques which are wellknown in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 77–96 (1985)). Such antibodies can be used to identify the presence of β(1–3)-glucans.

Kits useful in the methods and assays described above are also contemplated in the invention. Such a kit comprises primarily the components and reagents described for the methods and assays, such as a solid phase, detectable labels, β(1–3)-glucan binding agent, and/or labeled, underivatized, aqueous soluble, β(1–3)-glucan. In one embodiment, the kit comprises lactosyl ceramide, galactosyl ceramide, globotriaosylceramide, and/or asialoganglioside-GM1 as a β(1–3)-glucan binding agent. In a preferred embodiment, the β(1–3)-glucan binding agent is attached to a solid support, such as a filter, a membrane such as cellulose or nitrocellulose, a plastic support (e.g., microtiter plate, dipstick), a glass support (e.g., slide), beads (e.g., latex beads), particles, an organic resin, or other organic or non-organic solid phase.

The following Examples are offered for the purpose of illustrating the present invention and are not to be construed to limit the scope of this invention. The teachings of all references cited herein are incorporated herein by reference.

EXAMPLES

Example 1 Identification of Lactosyl ceramide as a binding agent for β(1–3)-glucan A. Materials Lactosyl ceramide was purified from human leukocyte membranes (HLM) as described below. All other sphingolipids, ceramides, and phospholipids were from Sigma Chemical Co. (St. Louis, Mo.), except lactosyl ceramide (porcine) which was from Matreya, Inc. (Pleasant Gap, Pa.). SOLVABLE™ was from DuPont (Boston, Mass.). 96-well polystyrene plates were from Corning (New York).

To prepare radioactively labeled underivatized, aqueous soluble β(1–3)-glucan, underivatized, aqueous soluble β(1–3)-glucan (PGG-Glucan, 17 mg; HPD0144, Alpha-Beta Technology, Worcester, Mass.) was incubated with $NaIO_4$ (225 mg; Sigma, St. Louis, Mo.) in sterile pyrogen-free (SPF) water for 72 hours at room temperature. The periodate was quenched by the addition of 50 mg glycerol. The underivatized, aqueous soluble β(1–3)-glucan was dialyzed against SPF water, and then reductively labeled with 100 mCi of $NaB^3H_4$ (New England Nuclear, Boston, Mass.). Radioactively labeled underivatized, aqueous soluble β(1–3)-glucan was separated from tritiated low molecular weight by-products by dialysis (10 K cut-off) and ultrafiltration. Purity of the labeled product was assessed by gel permeation chromatography.

B. Preparation of Human Neutrophils

Fresh whole blood was obtained from normal human volunteers using acid citrate dextrose as an anticoagulant. Following dextran sedimentation, cells were centrifuged (400×g, 7 minutes) and resuspended in autologous plasma. Cells were then layered over a Ficoll gradient (Lymphocyte Separation Medium; Organon Teknika, Durham, N.C.) and centrifuged (400×g, 30 minutes). Cells recovered from the pellet were hypotonically lysed to remove residual RBC. The remaining cells were greater than 95% neutrophils as judged by morphological criteria.

C. Preparation of Human Leukocyte Membranes

Buffy coat cells from human donors (Red Cross, Dedham, Mass.) were incubated in 3% dextran for 15–20 minutes at room temperature to separate leukocytes from red cells. The leukocyte-rich supernatant was pelleted (500×g, 7 minutes)

and washed once in ice cold phosphate buffered saline (PBS; Life Technologies, Grand Island, N.Y.). All subsequent operations were performed at 4° C. The remaining red cells were removed by hypotonic lysis, and the leukocytes recovered by centrifugation (850×g, 7 minutes). The cell pellet was resuspended in approximately 3–4× volume PBS, and protease inhibitors were added (5 mM EDTA, 40 μg/ml aprotinin, 1 μM pepstatin A, 1 μg/ml leupeptin, 50 μM PMSF). The cells were disrupted by probe sonication (50 watts, 30×1 second pulses). Disruption of cells was monitored microscopically. Nuclei and remaining intact cells were removed by low speed centrifugation (700×g, 7 minutes). Occasionally, the low speed pellet was resonicated and subjected to another low speed centrifugation. The low speed supernatants were then collected by high speed ultra-centrifugation (180,000×g, for 1 hour). Membrane pellets were resuspended in Hanks' balanced salt solution containing $Ca^{++}$ and $Mg^{++}$ (HBSS). Membrane protein was determined using the BCA or Comassie method (Pierce, Rockland, Ill.). Bovine serum albumin (Sigma, St. Louis, Mo.) was added to 1 mg/ml from a 10× stock, and the membranes stored in liquid nitrogen at 4–5 mg/ml. In some cases membranes were stored frozen without added protein; however, no change in binding was observed as a result of the different storage conditions.

In some cases, fresh human leukocytes were prepared from whole blood collected in acid citrate dextrose. Red blood cells were removed by dextran sedimentation and the leukocyte-rich layer was harvested and treated as described above. Finally, purified neutrophil and mononuclear leukocytes (including monocytes and lymphocytes) were prepared by resuspending the leukocyte-rich layer of cells in autologous plasma and layering the cells over Lymphocyte Separation Medium (LSM; Organon Technika) followed by centrifugation (700×g, 30 minutes). The neutrophil enriched pellet and the mononuclear cells present at the density interface were washed in ice cold PBS and membranes were prepared as described above. A stained Cytospin (Shandon) preparation indicated that the neutrophil preparation was greater than 95% pure, and that the mononuclear preparation contained approximately 40%-50% monocytes.

D. Preparation of Membranes from Cell Lines

Non-adherent cell lines (U937 (Deposit CRL-1593) and HL-60 (Deposit CCL-240), American Type Culture Collection (ATCC), Rockville, Md.) were collected by centrifugation (500×g, 7 minutes), washed in ice cold PBS, and the membranes were prepared as described above. Lightly adherent cell lines were washed with ice cold PBS and removed by gentle scraping with a cell scraper (Costar). Greater than 90% of the cells maintained viability during this procedure as determined by dye exclusion. Cells were resuspended in PBS and protease inhibitors. Tightly adherent cells were washed with ice cold PBS, then incubated with PBS plus the protease inhibitors described above. Cells were then removed by scraping and collected by centrifugation (500×g, 7 minutes). Membranes from adherent cells were then prepared as described above.

E. Extraction of Membranes with Chloroform/Methanol/Buffer

Human leukocyte membranes (5 mg protein/ml) prepared as described above were vortexed with 5 volumes of 3:2 chloroform/methanol (by volume) and centrifuged at 1,500×g to separate phases. The upper aqueous and lower organic phases were removed from the proteinaceous interphase, combined, and concentrated under a stream of Argon to approximately 50 μl. The residue was resuspended in HBSS, sonicated briefly, and centrifuged (12,000×g, 10 minutes) to pellet membranes. The pellet was resuspended in 500 μl HBSS and 100 μl was used per 350 μl binding assay. Assays for protein using the BCA reagent (Pierce) indicated that approximately 85% of the protein was removed from the resuspended fraction.

F. Purification of Lactosyl Ceramide (LacCer) from Human Leukocyte Membranes (HLM)

1. Extraction of Membranes with Chloroform/Methanol/Buffer

HLM (15 mg protein) in 1 mL of HBSS were extracted with chloroform (3 mL) and methanol (2 mL) by vortexing for one minute, followed by centrifugation at 1500×g for 10 minutes to separate the layers. The upper layer and proteinaceous interphase were discarded. The lower layer was dried under a stream of argon, and resuspended in 200 μL chloroform/methanol (10:1).

2. Thin Layer Chromatography Analysis of LacCer

Samples to be analyzed were spotted onto HPTLC silica gel plates and run in chloroform/methanol/water (80:20:2), along with commercially available LacCer standards. LacCer was visualized with the orcinol spray reagent (Schnaar, *Methods in Enzyrnology* 230:380 (Academic Press, 1994).

3. Silica Gel Chromatography

100 μL of the above extract was applied to a silica gel column (2 mL, 60 angstroms, 200–400 mesh) equilibrated in chloroform. The column was washed with chloroform (8 mL), then acetone (16 mL), followed by elution of a glycosphingolipid fraction with acetone/methanol (9:1, 16 mL). The acetone/methanol fraction was concentrated to dryness, and resuspended in acetone/methanol (10:1).

4. DEAE-Sephadex Chromatography

The acetone/methanol fraction from silica chromatography was applied to a DEAE-Sephadex A-25 column (1 mL resin in the acetate form, prepared in chloroform/methanol (1:2)). The column was washed with 60 mL chloroform/methanol (1:2). Neutral glycosphingolipids were contained in this fraction, which was dried and resuspended in chloroform/methanol (5:1).

5. Final Silica Gel Chromatography

Fractions from DEAE-Sephadex were applied to a Silica gel column (25×0.8 cm) equilibrated in chloroform. The column was washed with chloroform (60 mL), then chloroform/methanol (7.5:1) (60 mL). LacCer was eluted with chloroform/methanol (5:1) (60 mL), then chloroform/methanol (2:1) (60 mL).

6. HPLC Fractionation

Fractionation of LacCer into individual components was carried out on a Hewlett Packard 1090 HPLC using a reverse-phase Symmetry C18 column (3.9×150 mm, Waters Associate, Milford, Mass.) and a mobile phase of 3.5% 0.2 M ammonium acetate in methanol at a flow rate of 1 mL/min. Peaks with u.v. absorbance at 206 nm were collected, dried down, and analyzed by TLC to identify fractions containing LacCer. Isolated fractions were quantitated using a S.E.D.E.R.E. Sedex 55 evaporative mass detector (Alfortville France) at 45° C.

7. GC-MS Analysis

Three different analyses were performed on each isolated LacCer fraction. An aliquot was methanolyzed and the methanol solution extracted with hexane. The extracted fatty-acid methyl esters were analyzed by GC-MS (Irie et al., *J. Biochem* 108: 531–536 (1990). The methanol layer was dried, trimethylsilylated, and dissolved in hexane. The resulting trimethylsilylated methyl glycosides were analyzed by GC-MS (Irie et al., 1990). A second aliquot was treated with ceramide glycanase (see below) and freeze dried. The resulting acylated sphingosine and oligosaccharide were trimethylsilylated, dissolved in hexane, and analyzed by GC-MS on a HT-5 aluminum-clad capillary column.

G. Binding Assay in Reconstituted Membranes

Membranes were prepared from the receptor-negative cell line, U937 (Deposit CRL-1593, American Type Culture Collection (ATCC), Rockville, Md.) and extracted with chloroform/methanol as described above. The upper and lower layers were combined after removal of the proteinaceous interphase and dried under a stream of argon with the sample to be assayed for binding (lactosyl ceramide or fractions from the purification).

Alternatively, a mixture of purified phospholipids were dried with the sample for use in the binding assay. The phospholipid mixture contained phosphatidylcholine (132 μg), phosphatidylethanolamine (112 μg), phosphatidylinositol (36 μg), and phosphatidylserine (56 μg).

The dried lipid/sample preparations were resuspended in HBSS (500 μL) by brief sonication, and centrifuged for 10 minutes at 12,000×g. The supernatants from this spin were discarded, and the pellets were resuspended in HBSS (560 μL). Aliquots of 280 μL were added to tubes containing saline (35 μL) or unlabelled, underivatized, aqueous soluble β(1–3)-glucan (35 μL of 10 mg/mL stock), and $^3$H-underivatized, aqueous soluble β(1–3)-glucan (35 μL of a 10 μg/mL stock). Assays were incubated at 37° C. for one hour, after which time three 100 μL aliquots were removed and centrifuged in microfuge tubes at 12,000×g for 5 minutes at room temperature. The supernatants were discarded and the pellets were rinsed with 150 μL of HBSS. Pellets were then dissolved in SOLVABLE™, scintillation fluid was added, and radioactivity was measured.

H. Binding Assay in 96-Well Plates

Lactosyl ceramide or the sample to be measured was suspended in ethanol. Aliquots as specified were added in triplicate to the wells of a 96-well plate and air dried. The following components were premixed, then 100 μL was added to each well: saline (10 μL) or unlabelled, underivatized, aqueous soluble β(1–3)-glucan (10 μL of a 10 mg/ml stock), $^3$H-underivatized, aqueous soluble β(1–3)-glucan (10 μL of a 10 μg/ml stock), and HBSS (80 μL). Plates were incubated at 37° C. for 1.5 to 2 hours, then supernatants were removed from each well and discarded. Wells were rinsed with HBSS (200 μL) and SOLVABLE™ (100 μL) was added. The plate was incubated at 60° C. for 5 minutes, then supernatants were removed and counted.

I. Binding Assay—Leukocyte Membranes Oil/Sucrose Method

Membranes were diluted to 2 to 5 mg/ml in HBSS with and without 1 mg/ml BSA. The reaction mixture consisted of 280 μl membranes (2–4 mg/ml final concentration), 35 μl saline or test sample (in various concentrations), and 35 μl radioactively labeled underivatized, aqueous soluble β(1–3)-glucan (1 μg/ml final concentration). Binding was allowed to proceed for 60 to 120 minutes at 37° C. At the end of the incubation, 100 μl aliquots of reaction mixture were layered on top of a double layer density gradient consisting of 100 μl dibutyl phthalate (lower layer) and 100 μl 8% sucrose in PBS (upper layer) in 400 μl centrifuge tubes (Brinkman). The tubes were spun at 15,000×g for 4–5 minutes and the tips containing the membrane pellets were removed, incubated in 300 μl SOLVABLE™ (New England Nuclear, Boston, Mass.) overnight at 50° C. to dissolve the pellet, and then radioactivity determined by liquid scintillation counting. No radioactivity was found in the oil layer in the absence of added membranes. Alternatively, membranes were centrifuged directly in their incubation tubes at 15,000×g for 4–5 minutes at 37° C., the pellet washed with HBSS, then pellets solubilized and radioactivity determined by liquid scintillation counting.

Non-Oil/Sucrose Method

An alternative procedure to that using the oil/sucrose gradient involved centrifuging 100 μl aliquots of the binding assay in microfuge tubes at 12,000×g, for five minutes, followed by rinsing the resultant pellet with HBSS. Pellets were then dissolved in SOLVABLE™ and radioactively determined as above.

J. Generation of Monoclonal Antibodies to PGG Glucan

Balb/c female mice, aged 6 weeks (Charles River, Wilmington, Mass.) were used to generate monoclonal antibodies. Four mice were injected subcutaneously with 25 μg of very high molecular weight β(1–3)-glucan (Alpha-Beta Technology, Inc., Worcester, Mass.) which had been mixed 1:2 with TITERMAX™ adjuvant (Sigma, St. Louis, Mo.). After three weeks, plasma samples were collected and assayed for the presence of antibodies to β(1–3)-glucan by a direct ELISA screening protocol, as follows: 100 μl of a 10 μg/ml solution of PGG-glucan (Alpha-Beta Technology, Worcester, Mass.), or mannan (Sigma, St. Louis, Mo.) in phosphate buffered saline (PBS, Sigma, St. Louis, Mo.) was added to polystyrene Universal Binding microtiter plates (Corning Costar, Cambridge, Mass.) and incubated at room temperature for 1 hour. The plates were decanted and exposed to ultraviolet irradiation (1200 microjoules) for five minutes to facilitate cross-linking to the polystyrene. The plates were blocked with 1% gelatin (Difco, Detroit, Mich.) in PBS for 1 hour at 37° C., and decanted. A sample of cell culture supernatant was added to a PGG-glucan-coated plate and to a mannan-coated plate. Cell culture media (RPMI 1640, Sigma, St. Louis, Mo.) was used as the negative control. The sample were incubated for 1 hour at 37° C. then washed 5 times with PBS. Goat anti-mouse IgA, IgG, and IgM conjugated to horseradish peroxidase (Kirkegaard and Perry Labs, Gaithersburg, Md.) was diluted 1:1000 in 50% fetal bovine serum (FBS, Sigma, St. Louis, Mo.) in Tris/HCl buffer (Sigma, St. Louis, Mo.). The samples were incubated for 1 hour at 37° C., then washed 5 times with PBS. o-phenylenediamine dihydrochloride (Sigma, St. Louis, Mo.) was added and the plates were incubated 5–10 minutes at room temperature until strong color developed. $H_2SO_4$ (1 N) was added to each well to stop the reaction, and the color development was read in a spectrophotometer set to an optical density (OD) of 492 nm. A positive result was determined to be an OD reading on the PGG-glucan-coated plate which was at least twice the OD of the mannan-coated plate and the negative control.

One mouse had a moderate titer. This mouse was injected intravenously with 25 μL of VHMW β(1–3)-glucan in saline. Three days later, the spleen was removed, and a fusion with Sp2/0 mouse myeloma cells (Deposit CRL-1581, American Type Culture Collection (ATCC), Rockville, Md.) was performed (Lane, R. *J. Imm. Meth.* 81:223–228 (1985). Hybridomas were screened two weeks after fusion, by the direct ELISA screening protocol described above. Thirteen of 251 hybridomas were positive in the ELISA screening protocol and were isolated for expansion and cloning. After expansion, the remaining viable hybridomas were retested; positive clones were isotyped with a kit (Sigma, St. Louis, Mo.) and all proved to be IgM. The hybridomas were cloned, subcloned, and ascites fluid was produced (Mishell and Shiigi, *Selected Methods in Cellular Immunology*, W. H. Freeman and Co., San Francisco, Calif., 1980). The antibodies produced included four antibodies that were identified as PGG-Glucandetection antibody (BfD) I, BfD II, BfD III, and BfD IV (used in Example 2, below).

Example 2 GalCer Capture and Antibody Detection of β-Glucans in Biological Fluids Galactocerebroside Type II (Gal-Cer II) from bovine brain (Sigma, St. Louis, Mo.) was dissolved in 200 proof ethanol to a stock solution at a concentration of 1 mg/mL, rediluted 1:10 in ethanol, and sonicated before use. Sterile polystyrene 96-well ELISA microtiter plates (Corning Costar, Cambridge, Mass.) were coated with 20 μL per well of 0.1 mg/ml Gal-Cer II per well, and the ethanol was allowed to evaporate until dry. 150 μL of a blocking solution of Tris-buffered saline (TBS 0.05 M Tris-HCl, 0.15 M NaCl, both obtained from J. T. Baker (Phillipsburg, N.J.)) and 1% bovine serum albumin (Sigma, St. Louis, Mo.) was added to each well. The blocking solution was incubated at 37° C. for 30 minutes, or overnight at 4° C. Plates were decanted and blotted immediately prior to use.

Biological samples high in protein, such as serum, plasma, or cerebral spinal fluid (CSF) were treated with a de-proteinating step, such as standard trichloroacetic acid or perchloric acid precipitation methods (Obayashil, T., *J. Lab. Clin. Med.* 104(3):321–330 (1984). These samples were subsequently neutralized and concentrated to their original volumes. Alternatively, precipitation using a standard 70% ethanol precipitation method (*Methods in Enzymology Vol. 182: Guide to Protein Purification* (Deutscher, M. P., Ed., Academic Press, Inc, San Diego Calif., 1990), Chapter 22, pp. 285–306) was used to isolate analyte from proteinaceous biological fluids. Biological samples that did not have a high protein content, such as urine, needed no treatment.

To prepare a standard curve, underivatized, aqueous soluble β(1–3)-glucan (Alpha-Beta, Technology, Worcester Mass.), or other relevant underivatized, aqueous soluble β(1–3)-glucan was subjected to the same treatment that was required for the biological sample. The standard curve was a range of doubling dilutions from 10 ng/mL to 0.15 ng/mL as measured by hexose concentration of the purified glucan. The concentration of the glucan in the unknown was calculated using this standard curve.

Figure 3:
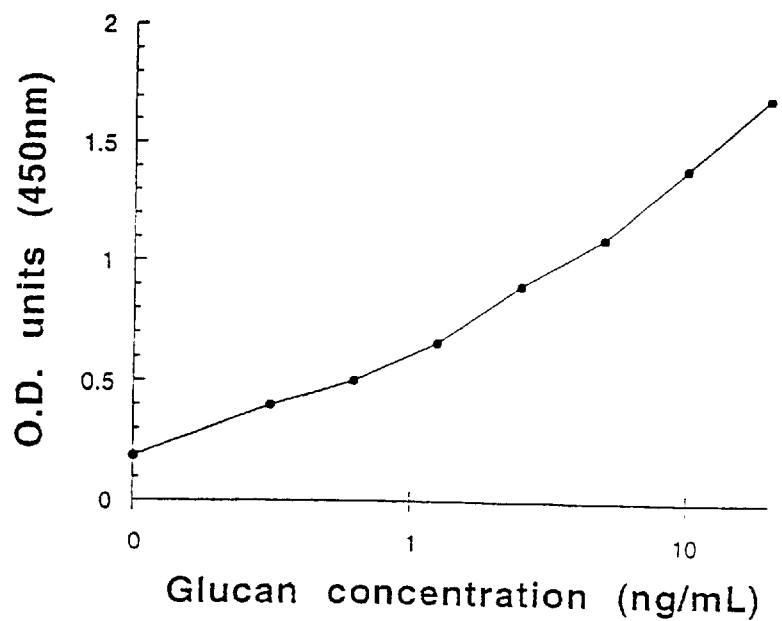
FIG. 3 is a graphic illustration of data showing that GalCer binds underivatized, aqueous soluble β(1–3)-glucan.

Biological samples (treated, if necessary, with a deproteinating step as described above) were added to the coated and blocked microtiter plate in volumes of 100 μl/well. The analytes were incubated 4–24 hours at 37° C. At the end of the incubation time, the plate was decanted and washed three times with TBS buffer (at least 350 μl/well). The monoclonal antibody, BfD IV (Alpha-Beta Technology, Worcester, Mass.) was diluted in blocking diluent to a concentration of 0.1 μg/mL and 100 μl was added to each well of the microtiter plate. The plate was incubated for 2 hours at 37° C. At the end of the incubation time, the plate was decanted and washed three times with TBS buffer (at least 350 μl/well). Previously titered, commercially available goat anti-mouse IgM antibody conjugated to horseradish peroxidase (Southern Biotechnology Associated, Birmingham, Ala.) was added, 100 μl/well (1:16,000), and incubated for 1 hour at 37° C. At the end of the incubation time, the plate was decanted and washed three times with TBS buffer (at least 350 μl/well). Tetramethylbenzidine (TMB), 0.4 g/L in an organic base (Kirkegaard & Perry Laboratories, inc., Gaithersburg, Md.) was added and incubated at room temperature for a previously established time (approximately 10 to 60 minutes) that was determined by cross-titering with various concentrations of the goat anti-mouse IgM antibody conjugation to horseradish peroxidase. Each well of the microtiter plate was read in a spectrophotometer at 450 nanometers to determine the optical density. The results, shown in FIG. 3, demonstrate the ability of GalCer to capture glucan.

Example 3 Comparison of μ(1–3)-Glucan Binding Agents

Figure 4:
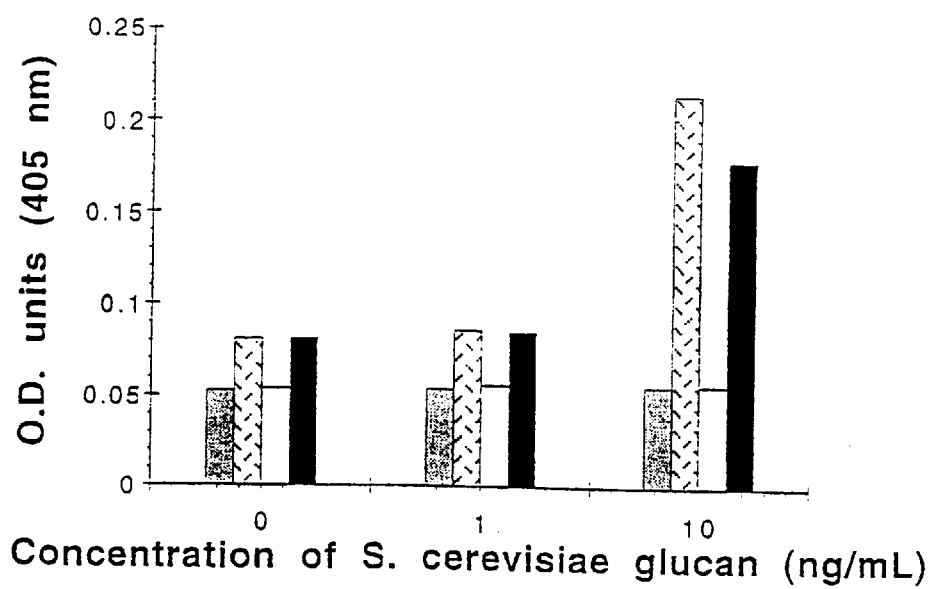
FIG. 4 is a graphic illustration of data showing that GalCer and LacCer bind significantly more underivatized, aqueous soluble β(1–3)-glucan in a 96-well plate assay, using Limulus amebocyte lysate as a detection agent, than does GlcCer. Negative control (grey boxes), GalCer (hatched boxes), GlcCer (open boxes), LacCer (solid boxes).

A comparative analysis of the ability of galactocerebroside (GalCer), glucocerebroside (GlcCer) and lactocerebroside (LacCer) to bind underivatized, aqueous soluble β(1–3)-glucan was conducted. 96-well plates were coated with 1 μg/well of a sphingolipid (GalCer, GluCer or LacCer) or with ethanol (negative control), blocked with 150 μl/well 1% gelatin (Difco, Mich.), and incubated with various concentrations of underivatized, aqueous soluble β(1–3)-glucan from Saccharomyces cerevisiae; subsequently, Limulus amebocyte lysate was added, and enzyme activation of Factor G was monitored (Morita, T et al., *FEBS Letters* 129:318–321 (1981); see also Tanaka, S. et al., *Carbohydrate Res.* 218:167–174 (1991); and Makami, T. et al., *Microbiol. Immunol.* 26(5):403–409 (1982), the entire teachings of which are incorporated herein by reference). Results, shown in FIG. 4, indicate that GalCer and LacCer bind significantly more underivatized, aqueous soluble β(1–3)-glucan at 10,000 pg/mL than GluCer or the negative control.

Example 4 Comparison of GalCer and LacCer β (1–3) Glucan Binding Agents

Figure 5:
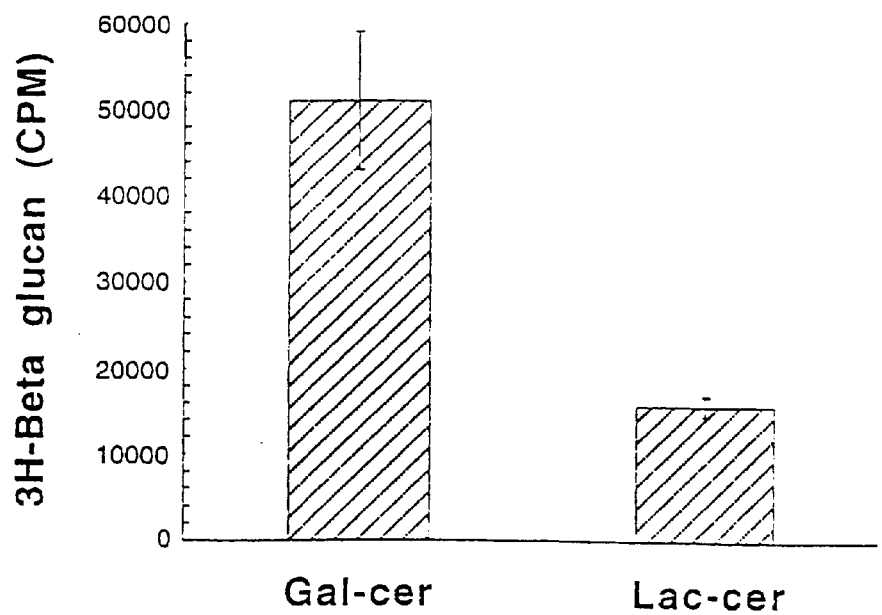
FIG. 5 is a graphic illustration of data showing that GalCer bound three times as much tritiated β(1–3)-glucan as LacCer in a capture experiment.

The ability of GalCer and LacCer to capture soluble β(1–3)-glucan was compared by coating a predetermined optimal concentration of either sphingolipid (20 μl or a 0.1 mg/ml solution) on a 96-well microtiter plate, and using a titrated preparation of glucan to detect the sphingolipid. Results, shown in FIG. 5, demonstrate that GalCer bound approximately three times as much titrated material as LacCer.

Figure 6:
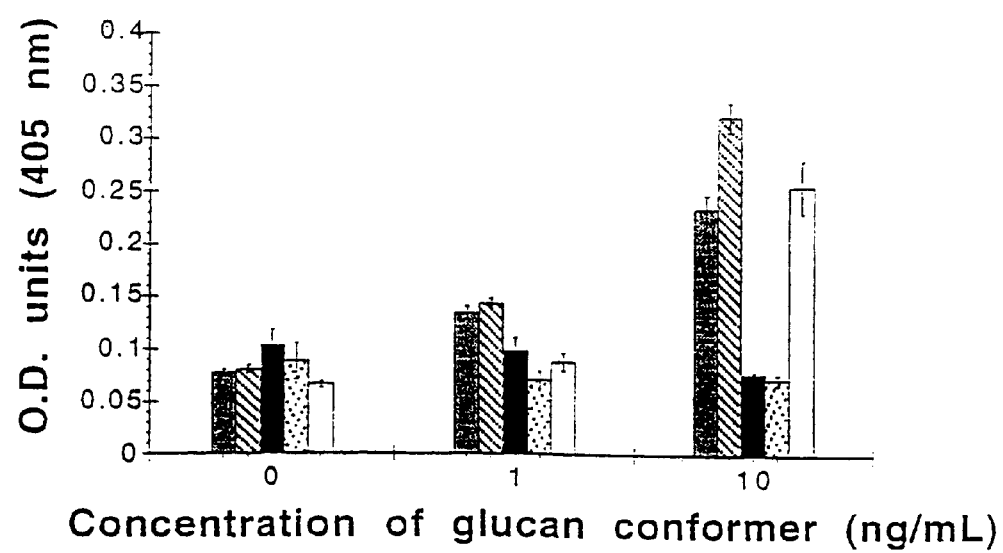
FIG. 6 is a graphic illustration of data showing the ability of GalCer to capture different conformational states of soluble β(1–3)-glucan. PGG-Glucan (open boxes), random coil glucan, (dotted boxes), single chain glucan (solid boxes), triple helix glucan (striped boxes), very high molecular weight glucan (shaded boxes).

Example 5 Ability of GalCer to Capture Different Soluble β(1–3)-glucan Aggregates An experiment was conducted to explore the ability of GalCer to capture various soluble β(1–3)-glucans, including PGG-Glucan (MOL WT=approximately 100,000), random coil glucan (molecular weight of approximately 6,000), single chain glucan (molecular weight of approximately 14,000), triple helix glucan (molecular weight of approximately 160,000) and very high molecular weight glucan (molecular weight of approximately 6,000,000). 96-well plates were coated with 2 μg/well 1% gelatin, and incubated with various concentrations of soluble β(1–3)-glucan aggregates from Saccharomyces cerevisiae; subsequently, Limulus amebocyte lysate was added, and enzyme activation of Factor G was monitored (Morita, T. et al., *FEDS Letters* 129:318–321 (1981)). The results, shown in FIG. 6, demonstrate that GalCer captures only glucans having high molecular weight (PGG-glucan, very high molecular weight glucan, and triple helix glucan).

Example 6 Identification of Aqueous Soluble Glucan in a Biological Matrix

A dilution series of crude preparation of an aqueous soluble glucan from *S. cerevisae* was added to normal human urine, to human plasma (+1-PCA treatment) and to Tris-buffered saline. The samples were assayed as described in Example 2, using GalCer, and a dilution curve generated.

Figure 7:
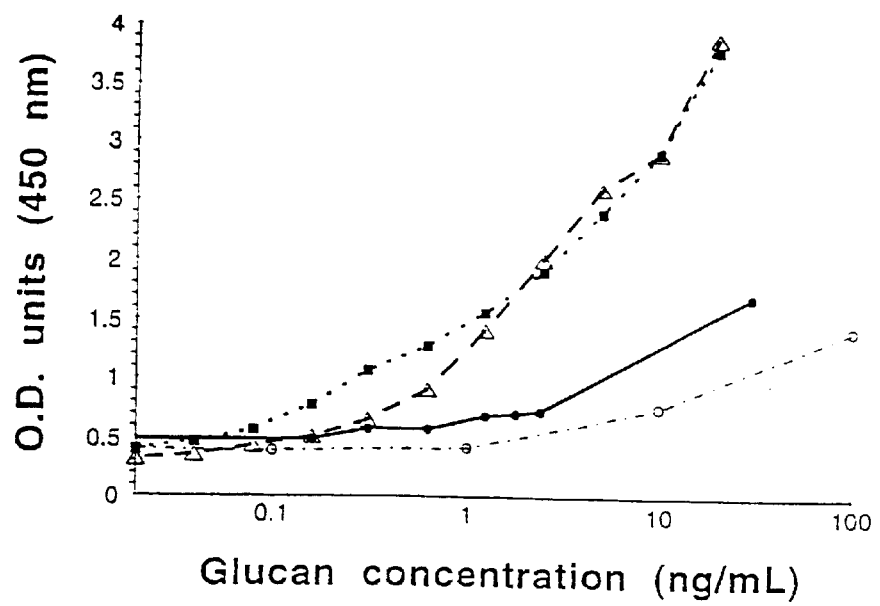
FIG. 7 is a graphic illustration of data showing the ability of GalCer to capture aqueous soluble glucan from *Candida albicans* in normal human urine (open triangles), human plasma (open circles), human plasma treated with PCA (closed circles) and buffer (closed squares).

The dilution curve, shown in FIG. 7, demonstrate that GalCer could capture the aqueous soluble glucan in urine, plasma and PCA-treated plasma, and allow its detection.

Example 7 Comparison of Sensitivity of β(1–3)-Glucan Antibodies

Figure 8:
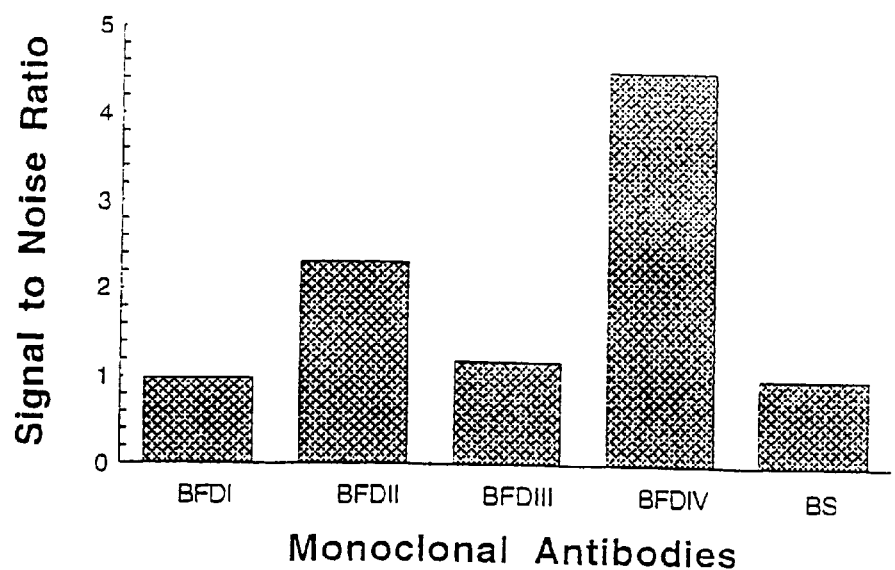
FIG. 8 is a graphic illustration of data showing that antibody BfD IV was most sensitive, when compared with antibodies BfD I, BfD II, BfD III, and a commercial antibody, in detecting soluble β(1–3)-glucan bound to GalCer.

A panel of monoclonal antibodies, generated as described in Example 1 (J), was used to detect soluble β(1–3)-glucan which had been bound to GalCer, as described in Example 2. BfD I, BfD II, BfD III, and BfD IV, as well as a commercially available antibody from B. Stone (Biosupplies, Parkville, Victoria, Australia), were used. The results, shown in FIG. 8, demonstrate the BfD IV was the most sensitive.

Example 8 Assessment of the Binding Capability of Antibody BfD IV

Various carbohydrate polymers were added to a competition ELISA to assess the specificity of the monoclonal antibody BfD IV. Polystyrene Universal Binding 96-well microtiter plates (Corning Coster) were coated with 100 μl of a 0.5 μl/mL solution of PGG-Glucan in phosphate-buffered saline (PBS from Sigma). The plate was incubated for 1 hour at 37° C., decanted and exposed to ultraviolet irradiation (1200 microjoules) for 5 minutes to facilitate cross-linking to the polystyrene. The plates were blocked with PBS plus 1% gelatin (Difco) for 30 minutes at 37° C. Two hundred μl of a 1/1000 dilution of monoclonal antibody BfD IV was mixed with the test compounds which were diluted in a range from 100-0.001 μg/mL. PGG-Glucan was included as a positive control test compound. The mixture was incubated for 1 hour at 37° C. The plates were washed 3 times with wash buffer consisting of PBS plus 0.1% Tween 20 (polyoxyethylenesorbitan monolaurate from Sigma) and 100 μl of the antibody-test compound mixture was added. The mixture was incubated on the plate for 2 hours at 37° C. The plates were washed three times and goat anti-mouse IgM conjugated to horseradish peroxidase (Kirkegaard and Perry Labs) was added and incubated for 1 hour at 37° C. The plates were washed three times and TMB (Kirkegaard and Perry Labs) was added and incubated for 5 minutes at room temperature. Stop solution (Kirkegaard and Perry Labs) was added and the color development was read on a spectrophotometer set to an optical density (OD) of 450 nm. Percent competition was determined by dividing the O.D. of the test compound (100 μg/mL concentration) by the O.D. of the PGG-Glucan positive control (100 μg/mL concentration) and multiplying the result by 100.

The results, shown in Table 4, demonstrate that BfD IV bound specifically to PGG-Glucan (BETAFECTIN™), triple helix conformer, VHMW conformer, laminaritetraose, laminaritriose, and partially bound to scleroglucan and pustulan.

TABLE 4

Binding Ability of BfD IV

| Compound | % Cross-reactive |
| --- | --- |
| PGG-Glucan[1] | 100 |
| Single Chain Conformer[1] | 0 |
| Random Coil conformer[1] | 0 |
| VHMW Conformer[1] | 100 |
| Chitobiose[2] | 0 |
| Curdlan[3] | 10 |
| Gentiobiose[4] | 0 |
| Endotoxin[4] | 0 |
| Glucosamine[4] | 0 |
| Scleroglucan[5] | 60 |
| Chitosan[6] | 0 |
| Pustulan[7] | 65 |
| Dextran[4] | 0 |
| Laminariheptaose[2] | 0 |
| Laminarihexaose[2] | 0 |
| Laminaripentaose[2] | 0 |
| Laminaritetraose[2] | 100 |
| Laminaritriose[2] | 100 |
| Laminaribiose[2] | 25 |
| Laminarin[4] | 0 |
| Glycogen[8] | 0 |
| Mannan[4] | 0 |

[1]Alpha-Beta Technology, Inc., Worcester, MA
[2]Seikagaku, Tokyo, Japan
[3]Wako, Osaka, Japan
[4]Sigma Chemicals, St. Louis, MO
[5]Sanofi Bio-industries, Paris, France
[6]JT Baker, Phillipsburg, NJ
[7]Calbiochem, La Jolla, CA
[8]ICN, Costa Mesa, CA

EQUIVALENTS

Those skilled in the art will recognize, or be able to ascertain, using no more than routine experimentation, many equivalents to the specific embodiments of the invention described herein. Such equivalents are intended to be encompassed by the following claims:

What is claimed is:

1. A method of isolating β(1–3)-glucan-containing organisms from a sample, comprising the steps of:

a. contacting a sample containing β(1–3)-glucan-containing organisms with a β(1–3)-glucan binding agent, under conditions that are suitable for binding of β(1–3)-glucan to the β(1–3)-glucan binding agent to form primary complexes of β(1–3)-glucan bound to β(1–3)-glucan binding agent;

b. isolating the primary complexes; and c. obtaining β(1–3)-glucan-containing organisms from the primary complexes.

2. A method of detecting the presence of β(1–3) glucan-containing organisms in a sample, comprising the steps of:

a. contacting a sample to be tested for the presence of β(1–3)-glucan-containing organisms with a β(1–3)-glucan binding agent, under conditions that are suitable for binding of β(1–3)-glucan, to the β(1–3)-glucan binding agent to form primary complexes of β(1–3)-glucan-containing organisms bound to β(1–3)-glucan binding agent; and b. detecting the primary complexes formed in step (a), wherein the presence of primary complexes is indicative of the presence of β(1–3)-glucan-containing organisms in the sample.

* * * * *